(12) United States Patent
Hasegawa

(10) Patent No.: US 9,063,068 B2
(45) Date of Patent: Jun. 23, 2015

(54) SHORT AXIS OSCILLATING ULTRASONIC PROBE

(75) Inventor: Yasunobu Hasegawa, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 1505 days.

(21) Appl. No.: 12/085,849

(22) PCT Filed: Feb. 16, 2007

(86) PCT No.: PCT/JP2007/053336
§ 371 (c)(1),
(2), (4) Date: May 30, 2008

(87) PCT Pub. No.: WO2007/105453
PCT Pub. Date: Sep. 20, 2007

(65) Prior Publication Data
US 2009/0048521 A1    Feb. 19, 2009

(30) Foreign Application Priority Data

Feb. 21, 2006   (JP) .................................. 2006-044558

(51) Int. Cl.
*A61B 8/14*    (2006.01)
*A61B 8/00*    (2006.01)
(Continued)

(52) U.S. Cl.
CPC ............... *G01N 29/2437* (2013.01); *A61B 8/12* (2013.01); *A61B 8/4281* (2013.01);
(Continued)

(58) Field of Classification Search
CPC .. A61B 8/4281; A61B 8/4461; A61B 8/4483; A61B 8/483; A61B 8/12; G10K 11/355; G01N 29/2437; G01N 29/265; G01N 29/28; G01N 29/32; G01N 29/221; B06B 1/0607

USPC .......................... 600/459, 446; 367/150, 188
See application file for complete search history.

(56) References Cited

U.S. PATENT DOCUMENTS 5,152,294 A * 10/1992 Mochizuki et al. ........... 600/459
5,460,179 A * 10/1995 Okunuki et al. .............. 600/444
(Continued)

FOREIGN PATENT DOCUMENTS

EP    0 432 771 A     6/1991
EP    0 432 771 A1    6/1991
(Continued)

OTHER PUBLICATIONS

European Search Report dated Mar. 30, 2009.
(Continued)

*Primary Examiner* — Long V Le
*Assistant Examiner* — Helene Bor
(74) *Attorney, Agent, or Firm* — Locke Lord LLP; Scott D. Wofsy; Christopher J. Capelli

(57) ABSTRACT

A short axis oscillating ultrasonic probe having a sealed container. A piezoelectric element group is housed within the sealed container and is arranged in a long axis direction. The piezoelectric group having an acoustic lens. The acoustic lens is provided on a rotational retention base which rotates and oscillates in the short axis direction of the piezoelectric element group. A projecting section is respectively provided on both end sides of the acoustic lens positioned in the long axis direction wherein each projection section includes an arc shape on a tip section thereof along a profile of an inner peripheral shape defined by a cover portion of the sealed container for absorbing unwanted ultrasonic waves that propagate in the long axis direction between the ultrasonic wave transmitting and receiving surface and an inner circumferential surface of the sealed container.

4 Claims, 6 Drawing Sheets

(51) Int. Cl.
    *G01N 29/00* (2006.01)
    *G01N 29/24* (2006.01)
    *A61B 8/08* (2006.01)
    *G01N 29/22* (2006.01)
    *G01N 29/265* (2006.01)
    *G01N 29/28* (2006.01)
    *G01N 29/32* (2006.01)
    *G10K 11/35* (2006.01)
    *A61B 8/12* (2006.01)

(52) U.S. Cl.
    CPC ............ *A61B 8/4461* (2013.01); *A61B 8/4483* (2013.01); *A61B 8/483* (2013.01); *G01N 29/221* (2013.01); *G01N 29/265* (2013.01); *G01N 29/28* (2013.01); *G01N 29/32* (2013.01); *G10K 11/355* (2013.01)

(56) References Cited

U.S. PATENT DOCUMENTS

| | | | |
|---|---|---|---|
| 6,277,077 B1 * | 8/2001 | Brisken et al. | 600/459 |
| 6,569,100 B2 * | 5/2003 | Okawa et al. | 600/445 |
| 7,081,093 B2 * | 7/2006 | Flesch | 600/459 |

FOREIGN PATENT DOCUMENTS

| | | |
|---|---|---|
| JP | 03 184532 A | 8/1991 |
| JP | Hei3-184532 | 8/1991 |
| JP | 09 037377 A | 2/1997 |
| JP | 2003-175033 | 6/2003 |
| JP | 1 736 767 A | 12/2006 |
| JP | 2006-346125 | 12/2006 |

OTHER PUBLICATIONS

International Search Report of PCT/JP2007/053336 mailed by the ISA on Jul. 17, 2007.

\* cited by examiner

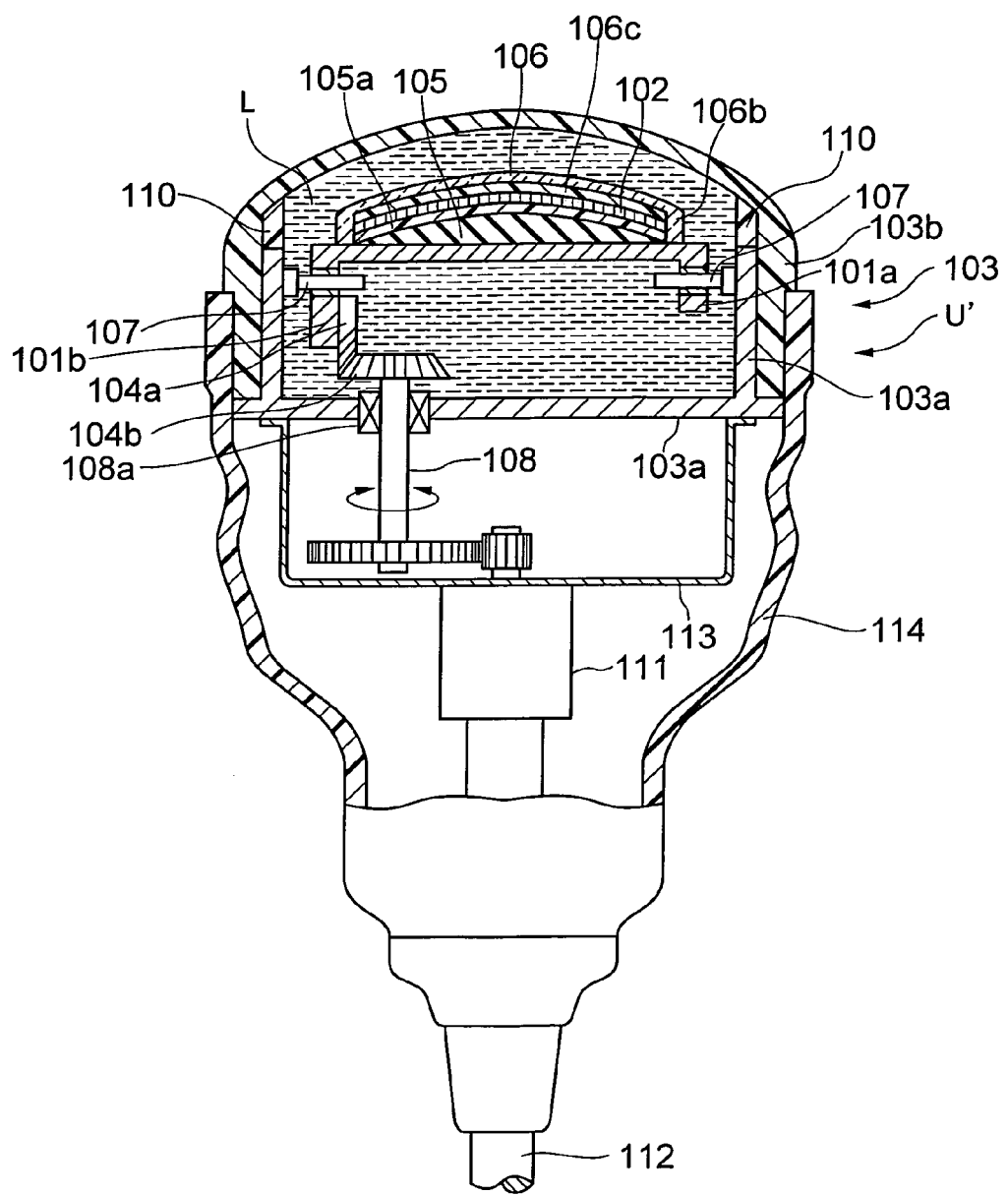

SHORT AXIS OSCILLATING ULTRASONIC PROBE

This application claims priority to PCT/JP2007/053336 filed Feb. 16, 2007, which claims priority to Japanese Patent Application No. 2006-044558 filed Feb. 21, 2006.

TECHNICAL FIELD

The present invention relates to a short axis oscillating ultrasonic probe (hereinafter, referred to as "short axis oscillating probe") that rotates and oscillates a piezoelectric element group in the short axis direction to obtain a three dimensional image of an examination subject, in particular, to a short axis oscillating probe in which unwanted ultrasonic waves propagating in the long axis direction, which is the arrangement direction of the piezoelectric elements, are absorbed.

BACKGROUND ART

Prior Art

A short axis oscillating probe is known as a probe that electronic scans a piezoelectric element group in the long axis direction thereof, and mechanically scans (oscillates) in the short axis direction thereof to obtain a three dimensional image of an examination subject. Consequently, such a probe has been brought to practical application because for example wiring (electrical connection) and scanning circuits thereof can be made simpler, compared for example to a matrix type ultrasonic probe in which piezoelectric elements are arranged in lengthwise and crosswise arrays to be electrically scanned in a two-dimensional direction.

(Prior Art) FIG. 3 is a drawing for explaining a conventional example of a short axis oscillating probe, wherein FIG. 3A is a sectional view in the long axis direction of the probe, and FIG. 3B is a sectional view in the short axis direction of the probe.

As shown in FIG. 3A, a short axis oscillating probe U' is such that a piezoelectric element group 102 provided on a rotational retention base 101 is housed within a sealed container 103. The rotational retention base 101 is of a sectionally channel shape with leg sections 101a and 101b on both end sides of a horizontal section thereof, and on the horizontal section there is provided the piezoelectric element group 102. Moreover, on the inner side face of the one leg section 101b there is fixed a first bevel gear 104a.

The piezoelectric element group 102 is configured such that a large number of piezoelectric elements 102a are arranged in the long axis direction. Here, the piezoelectric element group 102 is provided on the horizontal section of the rotational retention base 101, and it is fastened onto the top face of a backing member 105a, which is made of rubber or the like, on a base 105, the top face of which is of a curved surface. As a result, the ultrasonic probe is made as a so called convex type. On the surface of the piezoelectric element group 102, generally there is provided an acoustic matching layer 106c that brings acoustic impedance close to that of a living body (human body) to increase propagation efficiency, and on the top face of the acoustic matching layer 106c there is further provided an acoustic lens 106.

The thickness of the acoustic lens 106 is constant in the long axis direction, and as shown in FIGS. 3A, 3B, 4A, and 4B, the curvature of the acoustic lens 106 is such that the thickness is greatest in the center in the short axis direction. Furthermore a leg section 106b projects from the entire outer circumference of a curvature section 106a of the acoustic lens, and is attached so as to cover the outer circumference of the side face of the backing member 105a and the base 105. As a result, a focal point in the short axis direction is formed in the acoustic lens 106 to achieve efficiency of ultrasonic wave energy generated from the piezoelectric element group 102. The long direction of the piezoelectric element group 102 is electrically controlled.

Furthermore, as shown in FIG. 3A and FIG. 3B, the sealed container 103 is configured such that it has a structure for fitting to each other, a container main body 103a and a cover 103b, which are both sectionally concave shaped, thereby enabling free attachment and removal. On opposing side walls of the container main body 103a, there is fixed a pair of rotational center shafts 107 that rotate and oscillate the piezoelectric element group 102 in the short axis direction together with the rotational retention base 101, and the rotational center shafts 107 slidably engage with bearings of the leg sections 101a and 101b on both end sides of the rotational retention base 101. A rotation shaft 108 connected to a rotating mechanism such as motor passes through the bottom wall of the container main body 103a, and on the rotation shaft 108 there is provided a second bevel gear 104b so as to mesh with the first bevel gear 104a.

The rotating mechanism 111 such as a motor is covered by a back face cover 114 and is fastened onto a frame body 113, and a cable 112 to be connected to a diagnostic tool is led out from the back face cover 114. As a result, rotation of the second bevel gear 104b causes the first bevel gear 104a to rotate and oscillate in the short axis direction of the piezoelectric element group 102, and the rotational retention base 101 integrated with the first bevel gear 104a, and the piezoelectric element group 102, are thereby rotated/oscillated in the short axis direction.

Furthermore, in general, in order to prevent attenuation of the ultrasonic waves transmitted and received from the piezoelectric element group 102, a liquid that serves as an ultrasonic wave medium L such as oil is interposed between the surface of the piezoelectric element group 102 within the sealed container 103. Moreover, the inner circumferential side face of the cover 103b is coated with an ultrasonic wave absorbing member 110 made from a silicon resin or the like (approximately 2 to 3 mm) so as to absorb unwanted ultrasonic waves that propagate in the long axis direction between the surface serving as the ultrasonic wave transmitting and receiving surface of the piezoelectric element group 102 and the inner circumferential face of the surface of the cover 103b. As a result, a diagnostic image of an examination subject that has been formed can be made clearer while reducing noise.

If air is present between the inner circumferential surface of the cover 103b and the surface of the piezoelectric element group 102, attenuation of the ultrasonic waves becomes significant and propagation efficiency becomes degraded. As a result, it is not possible to perform excellent transmission and reception of ultrasonic waves. On the other hand, ultrasonic waves propagate through oil excellently, and the acoustic impedance of oil is 1.43 Mrayl (kg·cm$^3$/second), and thus comes close to the acoustic impedance of a human body 1.5 Mrayl. Therefore, the ultrasonic wave propagation efficiency can be increased. Here, unwanted ultrasonic waves in the long axis direction occur particularly in the case where the curvature is different between the inner circumferential surface of the cover and the convex curve of the piezoelectric element group.

(Japanese Examined Patent Publication No. Hei 7-38851, Japanese Unexamined Patent Publication No. 2003-175033, and Japanese Patent Application No. 2005-175700 (unpublished reference))

Problems in the Prior Art

However, in the conventional short axis oscillating probe configured as described above, as shown in FIG. 3A, a silicon resin serving as the ultrasonic wave absorbing member 110 is coated to a thickness 2 to 3 mm on the entire surface of the inner circumferential side surface of the cover 103b, resulting in a problem in that operation processes and an amount of work are involved. Moreover, in the case where an amount (area) of silicon resin application is large, for example, the silicon resin flows out and attaches to the opening end face of the cover 103b and causes a rough fitting with the container main body 103a, creating a gap therein. As a result, the level of sealing is impaired. On the other hand, in the case where the area of application is small, there has been a problem in that unwanted ultrasonic waves cannot be completely absorbed. Furthermore, since oil that serves as the ultrasonic wave medium L is filled within the sealed container 103, there has been a problem in that the weight of the short axis oscillating probe U' becomes greater, resulting in a reduced level of operability of the probe for a physician.

Object of the Invention

An object of the present invention is to provide a short axis oscillating probe that reduces manufacturing processes of the probe while achieving reliable sealing as well as absorption of unwanted ultrasonic waves, and that reduces the weight of the probe while achieving an excellent level of operability.

DISCLOSURE OF THE INVENTION

The present invention configures a short axis oscillating ultrasonic probe such that: a piezoelectric element group that is arranged in a long axis direction and that has an acoustic lens on an ultrasonic wave transmitting and receiving surface thereof is provided on a rotational retention base; the rotational retention base is housed within a sealed container so as to rotate and oscillate in a short axis direction of the piezoelectric element group; ultrasonic waves that are transmitted and received from the ultrasonic wave transmitting and receiving surface of the piezoelectric element group are mechanically scanned in the short axis direction; and a liquid that serves as an acoustic medium is filled within the sealed container; and has a means for absorbing unwanted ultrasonic waves that propagate in the long axis direction, between the ultrasonic wave transmitting and receiving surface and the inner circumferential surface of the sealed container. As the means for absorbing unwanted ultrasonic waves, a projecting section is provided on both end sides of the acoustic lens positioned in the long axis direction.

According to such a configuration, unwanted ultrasonic waves that propagate in the long axis direction of the piezoelectric element group are absorbed by the projecting section that functions as the ultrasonic wave absorbing means provided on both end sides of the acoustic lens. Consequently, due to this, a diagnostic image of an examination subject can be made clearer while reducing noise. Moreover, it is possible to exclude the process shown in the conventional example for applying a coating of an ultrasonic wave absorbing member such as silicon resin onto the inner circumferential side surface of the cover, thereby reducing the number of operation processes. Furthermore since the projecting section that serves as the ultrasonic wave absorbing means moves together with the rotation and oscillation of the piezoelectric element group in the short axis direction, unwanted ultrasonic waves can be reliably absorbed.

Moreover in the present invention: the rotational retention base has a leg section on both end sides of a horizontal section thereof and is of a sectionally channel shape; the sealed container comprises a container main body and a cover that are both concave shaped; and the side walls of the container main body have rotational center shafts that are provided in the long axis direction and that slidably engage with rotation shaft bearings provided in the leg sections of the rotational retention base. Furthermore, one of the leg sections of the rotational retention base has a first bevel gear that rotates/oscillates in the short axis direction of the piezoelectric element group, a rotation shaft passes in a sealed condition through a bottom wall of the sealed container, and the rotation shaft has a second bevel gear that meshes with the first bevel gear. As a result the piezoelectric element group can be rotated and oscillated in the short axis direction.

Furthermore since the ultrasonic wave absorbing means (projecting section) that serves as an ultrasonic wave absorbing means is integrally provided in the acoustic lens, sealing of the sealed container is not impaired as in the prior art due to the application of an ultrasonic wave absorbing member coating on the container main body or the inner circumferential side surface of the cover.

Moreover in the present invention, within the sealed container positioned below the rotational retention base, there is attached a light weight body, the relative density of which is smaller than that of the above mentioned liquid, and it is immersed in the liquid. As a result the entire weight of the probe can be made smaller compared to the case of completely filling the entire space within the sealed container with the liquid serving as an ultrasonic wave medium. As a result, an excellent level of operability of the probe for a physician can be realized.

Furthermore in the present invention, an interior of the light weight body that serves as an ultrasonic wave absorbing member is hollow. As a result, the relative density of the light weight body can be made even smaller than that of the liquid that serves as an ultrasonic wave medium.

BRIEF DESCRIPTION OF THE DRAWINGS

FIG. 1 is a drawing for explaining an embodiment of a short axis oscillating probe of the present invention, wherein

FIG. 2 is a drawing of an embodiment of an acoustic lens of the present invention, wherein

FIG. 3 is a drawing for explaining an embodiment of a short axis oscillating probe of a conventional example, wherein FIG. 3A is a sectional view in the long axis direction.

FIG. 4 is a drawing of an acoustic lens of the conventional example, wherein

BEST MODE FOR CARRYING OUT THE INVENTION

Figure 1A:
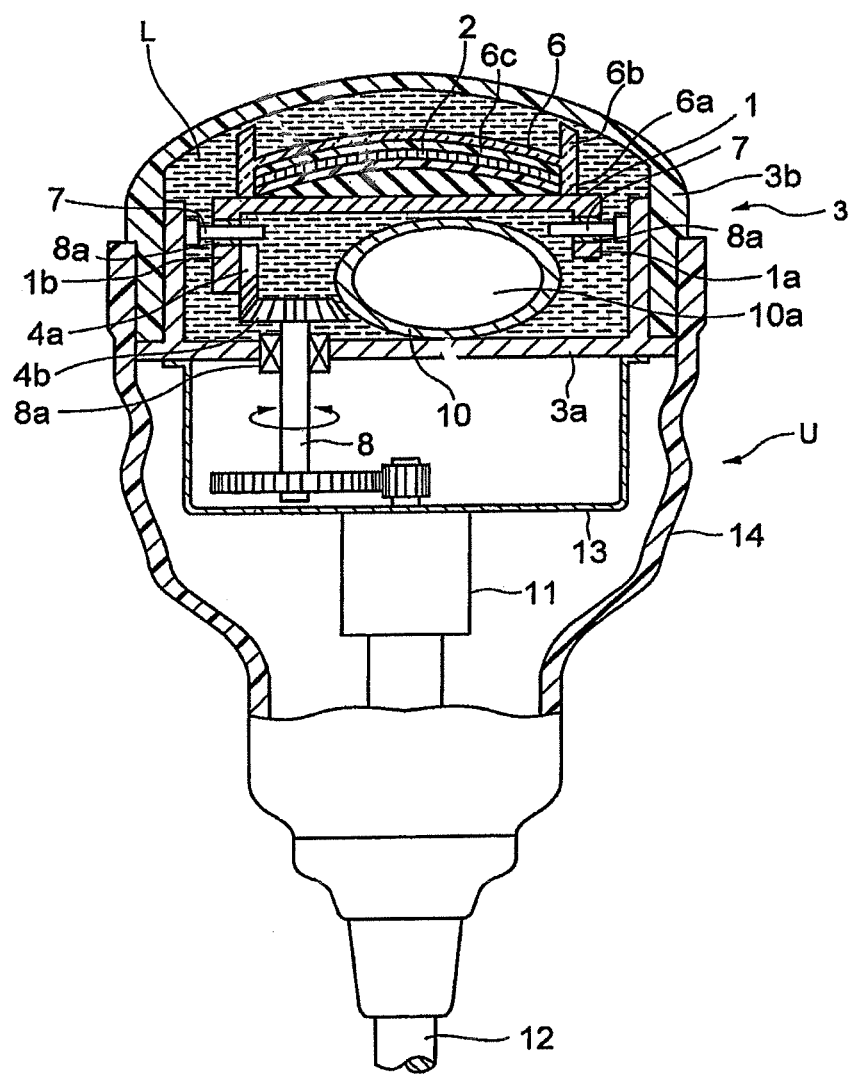
FIG. 1A is a sectional view in the long axis direction of a piezoelectric element group.
Figure 1B:
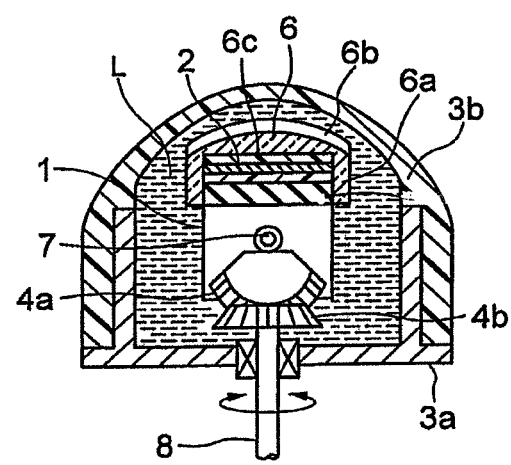
FIG. 1B is a sectional view in the short axis direction.
Figure 2A:
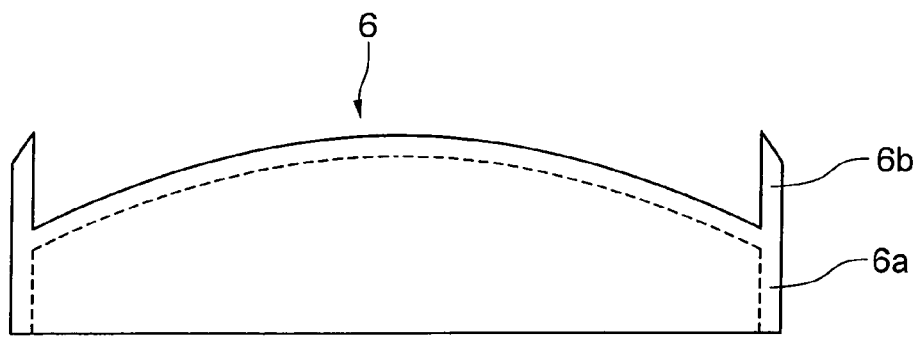
FIG. 2A is a front view in the long axis direction.
Figure 2B:
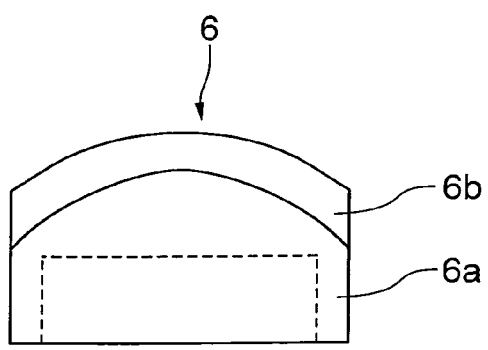
FIG. 2B is a side view in the short axis direction.
Figure 3B:
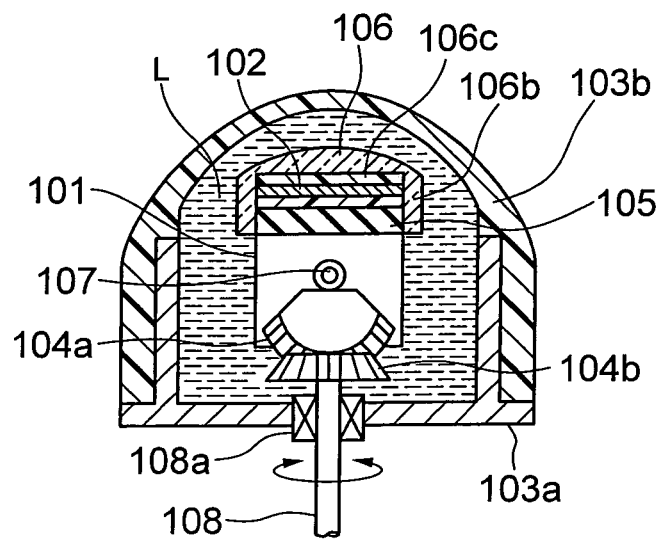
FIG. 3B is a sectional view in the short axis direction.
Figure 4A:
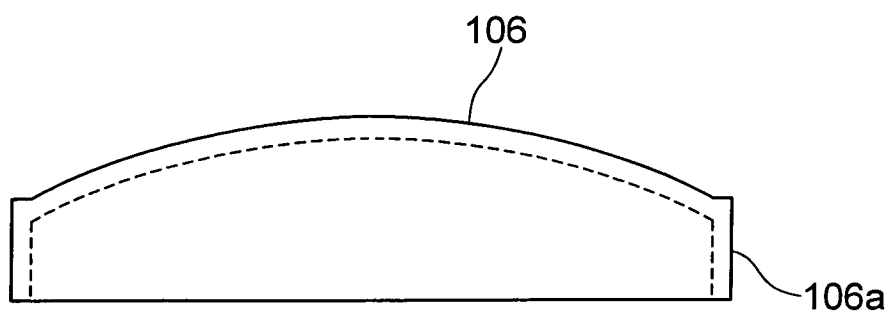
FIG. 4A is a front view in the long axis direction.
Figure 4B:
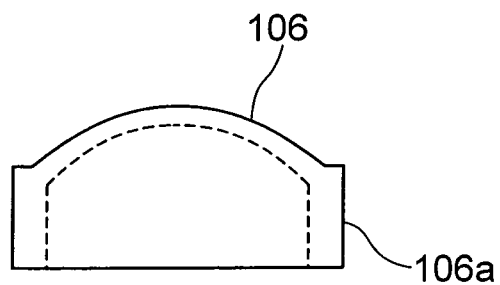
FIG. 4B is a side view in the short axis direction.

FIGS. 1A, 1B and FIGS. 2A, 2B are drawings for explaining an embodiment of an ultrasonic probe of the present invention. Here, FIG. 1A is a sectional view in the long axis direction and FIG. 1B is a sectional view in the short axis direction. FIG. 2A is a front view in the long axis direction and FIG. 2B is a side view in the uniaxial direction of the acoustic lens.

As shown in FIG. 1A, a short axis oscillating probe U of the present invention is such that a piezoelectric element group 2 that is arranged in the long axis direction and has an acoustic lens 6, is provided on a horizontal section of a sectionally channel shaped rotational retention base 1, and the piezoelectric element group 2 is housed within a sealed container 3 comprising a container main body 3a and a cover 3b that are both concave shaped. Leg sections 1a and 1b provided on both end sides of the rotational retention base 1 have bearings 8a with oil seals, and these bearings slidably engage with rotational center shafts 7 provided in the long axis direction in the side walls of the container main body 3a.

Moreover, as shown in FIG. 1B, a first bevel gear 4a that is provided on one of the leg sections 1b of the rotational retention base 1 so as to rotate and oscillate in the short axis direction, meshes with a second bevel gear 4b fastened onto a rotation shaft 8 that passes in a sealed condition though the bottom wall of the sealed container 3 and that is driven by a motor 11. As a result, the rotational retention base 1 and the piezoelectric element group 2 are rotated and oscillated in the short axis direction so as to mechanically scan in the short axis direction, ultrasonic waves transmitted/received from an ultrasonic wave transmitting and receiving surface of the piezoelectric element group 2. Inside the sealed container 3 is filled with a liquid that serves as a hyperacoustic medium L such as oil. Here, either one of the first bevel gear 4a and the second bevel gear 4b may be a plastic member instead of a metallic one to eliminate noise.

The rotating mechanism 11 such as a motor is covered by a back face cover 14 and is fastened onto a frame body 13, and a cable 12 to be connected to a diagnostic tool is led out from the back face cover 14.

Here as shown in particular in FIG. 2A and FIG. 2B, the acoustic lens 6 has leg section 6a that extends from the outer periphery of the curvature section thereof, and on its ultrasonic wave transmitting and receiving surface side on both end sides in the long axis direction, there is provided a projecting section 6b that serves as ultrasonic wave absorbing device. The tip end section of the projecting section 6b is of an arc shape along the profile of the inner peripheral shape of the cover 3b. Furthermore on the bottom wall of the container main body 3a, there is fastened, with a bonding agent or the like, a light weight body 10 having a hollow section 10a therein, and it is immersed in the oil of the ultrasonic wave medium L accommodated below the rotational retention base 1.

According to such a configuration, since the projecting section 6b that serves as an ultrasonic wave absorbing device is respectively provided on both end sides of the acoustic lens 6, unwanted ultrasonic waves that propagate in the long axis direction of the piezoelectric element group 2 are absorbed by this projecting section 6b. Consequently, a diagnostic image of an examination subject that has been formed can be made clearer while reducing noise.

As a result, a process of application of silicon resin or the like onto the inner circumference side surface of the cover shown in the conventional example can be omitted, and hence the number of operation processes required for manufacturing the probe can be reduced. Furthermore, since the silicon resin does not flow out during the course of the application process, the container main body 3a and the cover 3b are reliably bonded to each other, thereby achieving further reliable sealing within the container.

Moreover, the projecting section 6b that serves as an ultrasonic wave absorbing device is integrated with the piezoelectric element group 2. Therefore, they oscillate together with the rotation and oscillation of the piezoelectric element group 2 in the short axis direction. Consequently unwanted ultrasonic waves can be reliably absorbed. Furthermore, since the tip end side of the projecting section 6b is of an arc shape along the profile of the inner circumferential shape of the cover 3a, unwanted ultrasonic waves can be absorbed more efficiently.

Moreover as shown in FIG. 1A, within the container main body 3a positioned below the rotational retention base 1, there is provided the light weight body 10 that has the hollow section, the relative density of which is smaller than that of the oil serving as the ultrasonic wave medium L. Consequently, compared to the case of completely filling the space within the sealed container 3 with oil as practiced in the conventional example, the weight of the short axis oscillating probe can be made smaller. Therefore, an excellent level of operability of the probe for a physician can be realized.

In the above embodiment of the present invention, as shown in FIG. 2 the acoustic lens 6 has the leg section 6a extending from the entire periphery of the bottom surface of the curvature section thereof. However, the leg section 6a may be omitted and there may be only provided the curvature section. Moreover, as long as the relative density of the light weight body 10 is smaller than that of the ultrasonic wave medium, the form of the light weigh body 10 is not limited to a hollow body.

INDUSTRIAL APPLICABILITY

The short axis oscillating probe of the present invention can be widely used for forming a three dimensional image of an examination subject such as a human body.

The invention claimed is:

1. A short axis oscillating ultrasonic probe comprising:
   a sealed container having a short axis direction;
   a liquid that serves as an acoustic medium filled within said sealed container;
   a piezoelectric element group housed within the sealed container that is arranged in a long axis direction, said piezoelectric group having:
      an acoustic lens on an ultrasonic wave transmitting and receiving surface of the piezoelectric group, the acoustic lens having an inner surface facing the piezoelectric group, said acoustic lens provided on a rotational retention base which rotates and oscillates in said short axis direction of said piezoelectric element group whereby ultrasonic waves that are transmitted and received from said ultrasonic wave transmitting and receiving surface of said piezoelectric element group are mechanically scanned in said short axis direction; and
      a projecting section respectively fixed to both end sides of said acoustic lens and positioned in said long axis direction wherein each projection section includes an arc shape on a tip section thereof that is positioned above an outer surface of the acoustic lens and extends along a profile of an inner peripheral shape defined by a cover portion of said sealed container for absorbing unwanted ultrasonic waves that propagate in the long axis direction between said ultrasonic wave transmitting and receiving surface and an inner circumferential surface of said sealed container.

2. A short axis oscillating ultrasonic probe according to claim 1, wherein: said rotational retention base has a leg section on both end sides of a horizontal section thereof and is of a sectionally channel shape; said sealed container includes:
- a container main body and said cover portion that are both concave shaped wherein both side walls of said container main body have rotational center shafts that are arranged in the long axis direction and that slidably engage with rotation shaft bearings provided in the leg sections of said rotational retention base;
- a first bevel gear is provided on one of said leg sections of said rotational retention base whereby said first bevel gear rotates and oscillates in the short axis direction;
- a rotation shaft passes in a sealed condition through a bottom wall of said sealed container; and
- a second bevel gear that meshes with said first bevel gear is fastened onto said rotation shaft.

3. A short axis oscillating ultrasonic probe according to claim 1, wherein in said liquid within said sealed container positioned below said rotational retention base, there is immersed a light weight body, the relative density of which is smaller than that of said liquid.

4. A short axis oscillating ultrasonic probe according to claim 3, wherein an interior of said light weight body is hollow.

\* \* \* \* \*